United States Patent [19]

Asakura et al.

[11] Patent Number: 4,842,711
[45] Date of Patent: Jun. 27, 1989

[54] DEVICE FOR DETECTING AIR-FUEL RATIO OF ENGINE

[75] Inventors: Masahiko Asakura, Saitama; Tomohiko Kawanabe, Tochigi; Noritaka Kushida, Tokyo, all of Japan

[73] Assignee: Honda Giken Kogyo Kabushiki Kaisha, Tokyo, Japan

[21] Appl. No.: 124,377

[22] Filed: Nov. 20, 1987

Related U.S. Application Data

[63] Continuation of Ser. No. 865,568, May 21, 1986, abandoned.

[30] Foreign Application Priority Data

May 27, 1985 [JP] Japan .................... 60-113405

[51] Int. Cl.⁴ .................................. G01N 27/46
[52] U.S. Cl. ........................ 204/406; 204/412; 204/425; 204/1 T; 123/440; 123/489
[58] Field of Search ............. 204/406, 412, 425, 426, 204/427, 428, 1 T; 123/440, 489

[56] References Cited

U.S. PATENT DOCUMENTS 4,617,901 10/1986 Otobe .......................... 123/440
4,697,564 10/1987 Ohgami ........................ 123/440

Primary Examiner—John F. Niebling
Assistant Examiner—Ben C. Hsing
Attorney, Agent, or Firm—Lyon & Lyon

[57] ABSTRACT

A device for detecting the air-fuel ratio of an engine by measuring an oxygen concentration of the exhaust gas by means of an oxygen sensor including an oxygen pump and a cell element for measuring the oxygen concentration ratio, comprising an air-fuel ratio detecting circuit which reads the output signal of the oxygen sensor and effects the detection of the air-fuel ratio when TDC signal has been produced, depending upon the operation of the engine, and a time previously set by a timer has passed.

4 Claims, 2 Drawing Sheets

DEVICE FOR DETECTING AIR-FUEL RATIO OF ENGINE

This application is a continuation of application Ser. No. 865,568, filed 5/21/86, now abandoned.

BACKGROUND OF THE INVENTION

1. Field of the Invention

The present invention relates to a device for detecting air-fuel ratio of an engine in which an oxygen sensor of oxygen-concentration measuring type is used.

2. Prior Art

A prior art system of this kind is shown in FIG. 3. Use is made of an oxygen sensor of the oxygen concentration measuring type which includes oxygen-ion conductive and solid electrolyte materials 1 and 2, a spacer 3 made of inorganic heat-resistant adhesive material interposed between said electrolyte materials to partly form a restricted region, such as gap G, therebetween and a pair of opposing electrodes 4 and 5 arranged at the positions of said gap G, respectively, one of which constitutes an oxygen pump element 6 and the other of which constitutes a cell element 7 for measuring an oxygen concentration ratio. The air-fuel ratio of the engine is detected by measuring the oxygen concentration in the exhaust gas, for example.

Such oxygen sensor is positioned in the exhaust gas pipe and a D.C. voltage $V_B$ is applied between the electrodes 4 at the side of the oxygen pump element 6, with the polarity as shown in the drawing. Then, the oxygen ion passes through the solid electrolyte material 1 of the oxygen pump element 6 and the oxygen in the gap G leaks through said material to the outside. Accordingly, a difference in oxygen concentration occurs between the gap G and the outside so that an electromotive force E is produced by the cell element 7. At this time the electromotive force E produced by the cell element 7 is compared with a reference voltage by means of a comparator CMP and the pump current Ip fed to the oxygen pump element 6 is subjected to feed-back control so that $E = V_s$. Thus the oxygen concentration in the exhaust gas is obtained, depending upon the value of the pump current Ip which is obtained at this moment with a linear characteristic.

The output signal of the oxygen sensor produced at this time is proportional to the air-fuel ratio of the engine. For example, it is assumed that the reference voltage Vs is set at 40 mV. Then, if the variation of value of the output voltage converted from the value of the pump current Ip is within the range of 0~1.5 V, it is possible to detect the air-fuel patio of the engine within the range of 14.6~27 air-fuel ratio.

However, a problem resides in the case of detection of the air-fuel ratio of the engine by means of the oxygen sensor arranged in the exhaust pipe. That is, pulsations arise in the exhaust gas, depending upon the operation of the engine and thus a hunting arises in the output signal of the oxygen sensor, so that an error may be produced in the value of the air-fuel ratio of the engine detected on the basis of the output signal of the oxygen sensor. Particularly, in the case of a lean-burn engine, when the air-fuel ratio control is effected to hold the air-fuel ratio of the engine at a predetermined value, in accordance with the output signal of the oxygen sensor, the accuracy of the air-fuel ratio control is considerably reduced, owing to the error of the air-fuel ratio detected by the oxygen sensor having a linear characteristic in the lean-area.

OBJECT OF THE INVENTION

In view of the problem as described above, it is an object of the present invention to provide a device for detecting the air-fuel ratio of an engine by measuring the oxygen concentration of the exhaust gas by using an oxygen sensor in which the detection of the air-fuel ratio can be effected always in a stable manner, without being subjected to the influence of the hunting of the output signal of the oxygen sensor which is caused by the pulsation of the exhaust gas.

SUMMARY OF THE INVENTION

In order to attain the object as described above, the present invention provides a device for detecting the air-fuel ratio of an engine which comprises an air-fuel ratio detecting circuit arranged to read the output signals of the oxygen sensor at predetermined timings according to the operation of the engine, whereby the detection of the air-fuel ratio is effected on the basis of the output signals of the oxygen sensor which have been read at the predetermined timings.

DESCRIPTION OF THE PREFERRED EMBODIMENT

Now, an embodiment of the present invention will be explained in detail with reference to the drawings.

Figure 1:
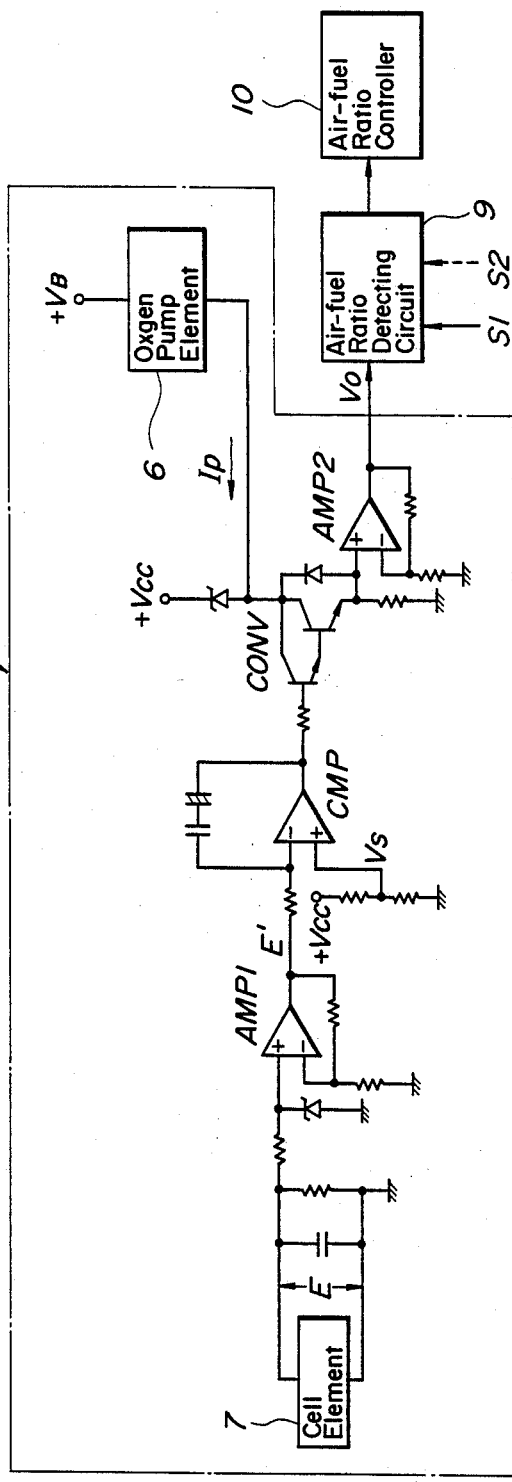
FIG. 1 is an electrical wiring diagram illustrating one embodiment of the device for detecting air-fuel ratio of the engine according to the present invention.

The device for detecting the air-fuel ratio of an engine, as shown in FIG. 1, comprises an oxygen sensor 8, an air-fuel ratio detecting circuit 9 and an air-fuel ratio controller 10. The air-fuel ratio detecting circuit 9 is arranged to read the output voltage Vo at predetermined timings depending upon the operation of the engine and detect the air-fuel ratio at that time.

An upper dead point signal (a so-called "Top Dead Center" or TDC signal) S1 of the engine is determined in any conventional manner, such as by a magnet on the flywheel or crankshaft and a pick-up coil on the cylinder block, to indicate a point in the rotation of the crankshaft when a cylinder is at its uppermost location, i.e., "Top Dead Center". This TDC signal is applied to the air-fuel detecting circuit 9. When a constant time ta, which had been preset in an internal timer, has passed after the TDC signal was obtained, a timing signal T for reading the output of the oxygen sensor is produced and the value of the output voltage Vo of the oxygen sensor 8 at this moment is read, thereby detecting the air-fuel ratio of the engine.

More particularly, the above device may be so arranged, for example, that an input gate is positioned in the air-fuel ratio detecting circuit 9 and it is opened by the read timing signal T, thereby reading the output of the oxygen sensor 8.

Figure 2:
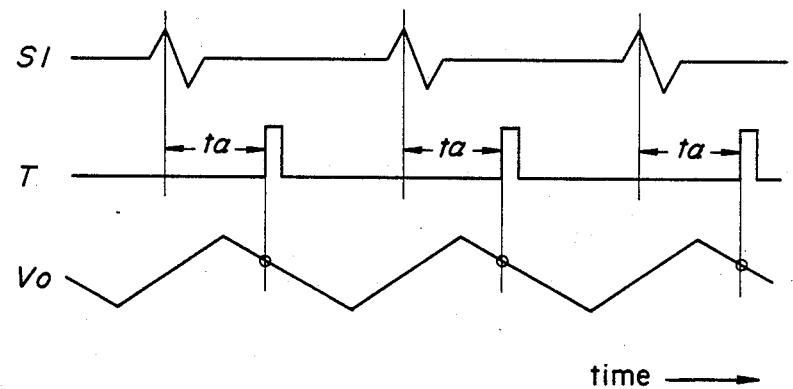
FIG. 2 is a time chart showing the timing of the respective signals in the device shown in FIG. 1.
Figure 3:
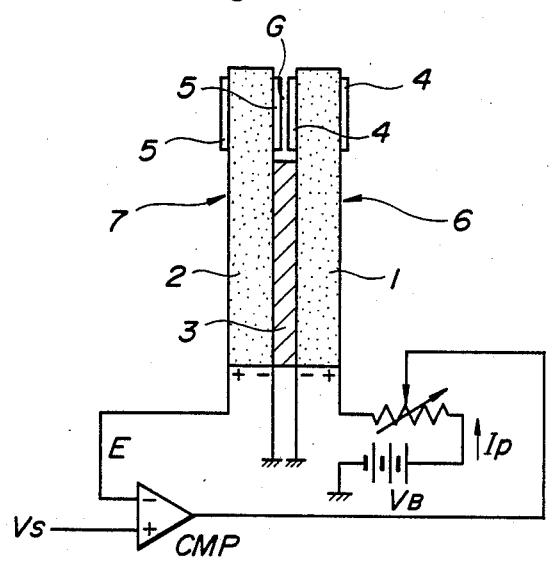
FIG. 3 illustrates the fundamental construction of the conventional oxygen sensor.

The hunting is normally produced in the output voltage Vo of the oxygen sensor 8 due to the pulsation of the exhaust, gas, depending on the operation of the engine. However, if the operation state of the engine is stable, the period of the hunting is substantially constant, as shown in FIG. 2 and, consequently, if the output voltage Vo of the oxygen sensor 8 is read at the predetermined timing corresponding to the operation or position of rotation of the engine a voltage which is always proportional to the output voltage Vo of the oxygen sensor 8 is obtained, without being subjected to the influence of the hunting thereof, so that the air-fuel ratio of the engine is detected, without producing error.

In the construction as shown in FIG. 1, the oxygen sensor 8 includes a cell element 7, an amplifier AMP 1 for amplifying the voltage E, a comparator CMP for comparing the amplified voltage E' with a reference voltage Vs, a voltage-current converter CONV for feeding the pump current Ip to an oxygen pump element 6 in which the pump current Ip is controlled so that E'=Vs, and an amplifier AMP 2 for converting the controlled pump current Ip into a voltage signal to produce the output voltage Vo. The detection signal corresponding to the air-fuel ratio of the engine detected by the air-fuel ratio detecting circuit 9 is fed to the air-fuel controller 10, for example, which controls the air-fuel ratio to a predetermined value.

It is possible to produce the read timing signal T in the air-fuel detecting circuit 9, on the basis of the operating crank angle of the engine.

It is also possible to provide the air-fuel detecting circuit 9, for example, with an operating a crank angle signal which corresponds to the angle of 60° preceding the upper dead point of the engine and to use said crank angle signal as the read timing signal T to read the output voltage Vo of the oxygen sensor 8.

In the embodiment as described above, the air-fuel ratio detecting circuit 9 is so constituted that when the output voltage Vo of the oxygen sensor 8 is read at the timing corresponding to the operation of the engine the time $t\alpha$ from the reception of the TDC signal S1 to the production of the read timing signal T is constant. In general, however, as the number of revolutions per unit of time (i.e., rpm) of an engine increases the pulsation of the exhaust gas tends to decrease, so that the degree of hunting of the output voltage Vo of the oxygen sensor 8 tends to decrease. Accordingly, more precise detection of the air fuel ratio can be effected if the time $t\alpha$ is made variable, depending upon the number of revolutions per unit of time of the engine.

In such case, a TDC signal S1 and a signal S2 corresponding to the number of revolutions per unit of time, i.e. the rotational speed Ne, of the engine are fed to the air-fuel ratio detecting circuit 9. The characteristic concerning the relation of $t\alpha \propto 1/Ne$ is previously stored in a memory, and the time $t\alpha$ may be selected to an optimum value, depending on the number of revolutions per unit of time of the engine Ne at that time.

As explained above, the present invention provides a device for detecting an air-fuel ratio of an engine in which at the time of detecting the air-fuel ratio of the engine by measuring oxygen concentration in exhaust gas by means of an oxygen sensor, the air-fuel ratio detecting circuit acts to read the output voltage of the oxygen sensor at a predetermined timing corresponding to the operating state of the engine and the detection of the air-fuel ratio is effected on the basis of the output signal of the oxygen sensor which has been read at the predetermined timing. Such construction provides a superior advantage that the detection of the air-fuel ratio is effected always in a stable manner, without being subjected to the influence of the hunting of the output signal of the oxygen sensor owing to the pulsation of the exhaust gas.

We claim:

1. A device for detecting an air-fuel ratio of an engine by measuring an oxygen concentration of an exhaust gas by means of an oxygen sensor including a pair of oxygen-ion conductive and solid electrolytic materials arranged in the gas to be measured, said solid electrolytic materials having electrodes formed on the surfaces thereof and being arranged in confronting relationship with each other with a predetermined restricted region therebetween, said restricted region being subject to the influence of pulsations existent in said exhaust gas, one of said solid electrolytic materials constituting an oxygen pump element and the other constituting a cell element that develops an electromotive force for use in measuring an oxygen concentration ratio, said device comprising means for applying a variable electromotive current to the oxygen pump element in response to variations in oxygen concentration for causing the cell element to generate a constant predetermined reference voltage, thereby detecting an air-fuel ratio of a mixed gas fed to the engine by means of a pump current value under such state that said oxygen concentration in said restricted region is held constant by feeding a variable current to the oxygen pump element so that a terminal voltage of the cell element becomes constant, means for producing an output signal of the oxygen pump, said output signal being subjected to variation as the result of variation of said oxygen concentration in said restricted region caused under the influence of said pulsation of said exhaust gas passing through said restricted region, and an air-fuel ratio detecting circuit which reads the output signal of the oxygen sensor and means for effecting the detection of the air-fuel ratio at a predetermined point in the engine operation following a TDC signal and a predetermined period previously set by a timer having passed after said TDC signal.

2. A device for detecting an air-fuel ratio of an engine according to claim 1, wherein said predetermined time period is changed in response to a rotational speed of the engine.

3. A device for detecting an air-fuel ratio of an engine according to claim 2, wherein said predetermined time period decreases with an increase in said rotational speed of the engine.

4. A device for detecting an air-fuel ratio of an engine by measuring an oxygen concentration of an exhaust gas by means of an oxygen sensor including a pair of oxygen-ion conductive and solid electrolytic materials arranged in the gas to be measured, said solid electrolytic materials having electrodes formed on the surfaces thereof and being arranged in confronting relationship with each other, with a predetermined restricted region therebetween, said restricted region being subjected to the influence of pulsations existent in said exhaust gas, one of said solid electrolytic materials constituting an oxygen pump element and the other constituting a cell element that develops an electromotive force for use in measuring an oxygen concentration ratio, said device comprising means for applying a variable electromotive current to the oxygen pump element in response to variations in oxygen concentration for causing the cell element to generate a constant predetermined reference voltage, thereby detecting an air-fuel ratio of a mixed gas fed to the engine by means of a pump current value under such state that said oxygen concentration in said restricted region is held constant by feeding a variable current to the oxygen pump element so that a terminal voltage of the cell element becomes constant, means for producing an output signal of the oxygen sensor related to the electromotive current applied to the oxygen pump, said output signal being subjected to variation as the result of variation of said oxygen concentration in said restricted region caused under the influence of said pulsation of said exhaust gas passing through said restricted region, and an air fuel ratio detecting circuit which reads the output signal of the oxygen sensor and means for effecting the detection of air-fuel ratio at a predetermined point in the operation of the engine following a period of time after a TDC signal has been produced, said period of time depending upon the operation of the engine and being previously set to a value which is in inverse proportion to the number of revolutions per unit of time of the engine after said TDC signal.

* * * * *